(12) United States Patent
Nagano et al.

(10) Patent No.: US 8,560,249 B2
(45) Date of Patent: Oct. 15, 2013

(54) DANGEROUS SUBSTANCE DETECTION SYSTEM

(75) Inventors: Hisashi Nagano, Nishitokyo (JP); Yasuaki Takada, Kiyose (JP); Minoru Sakairi, Tokorozawa (JP); Yuichiro Hashimoto, Tachikawa (JP); Masuyuki Sugiyama, Hino (JP)

(73) Assignee: Hitachi, Ltd., Tokyo (JP)

( * ) Notice: Subject to any disclaimer, the term of this patent is extended or adjusted under 35 U.S.C. 154(b) by 403 days.

(21) Appl. No.: 12/903,263

(22) Filed: Oct. 13, 2010

(65) Prior Publication Data

US 2011/0093214 A1  Apr. 21, 2011

(30) Foreign Application Priority Data

Oct. 15, 2009 (JP) .................. 2009-238438

(51) Int. Cl.
*G01N 31/00* (2006.01)
(52) U.S. Cl.
USPC .......................................................... 702/24
(58) Field of Classification Search
USPC .......................................................... 702/24
See application file for complete search history.

(56) References Cited

U.S. PATENT DOCUMENTS

| 6,894,276 B1 * | 5/2005 | Takada et al. ............... 250/292 |
| 2009/0038374 A1 * | 2/2009 | Broz ............................ 73/23.37 |

FOREIGN PATENT DOCUMENTS

| JP | 2000-028579 | 1/2000 |
| JP | 2004-125576 | 4/2004 |
| JP | 2008-157685 | 7/2008 |

OTHER PUBLICATIONS

Yamaguchi et al, "Gas chromatography/time-of-flight mass spectrometry of triacetone triperoxide based on femtosecond laser ionization", Rapid Communications in mass Spectrometry, Rapid Commun. Mass Spectrom., 2009; 23:3101-3106.
Burks; Current trends in the detection of peroxide-based explosives, Anal Bioanal Chem (Jul. 31, 2009) 395:301-313, DOI 10.1007/s00216-009-2968-5.
Rodriguez; "In Situ Trace Detection of Peroxide Explosives by Desorption Electrospray Ionization and Desorption Atmospheric Pressure chemical Ionization", Department of Chemistry, Purdue University, Anal. Chem 1008, 80, 1512-1519.

* cited by examiner

*Primary Examiner* — Stephen Cherry
(74) *Attorney, Agent, or Firm* — Antonelli, Terry, Stout & Kraus, LLP.

(57) ABSTRACT

A method of quickly detecting a handmade explosive in a bottle with a low erroneous alarm frequency is provided. A sample gas generated from a bottle placed on a bottle placement space is sucked-in, and ions of the sample gas are generated by an ion source and subjected to mass analysis. The presence/absence of a mass spectrum derived from the handmade explosive is determined from an obtained mass spectrum, and the result thereof is displayed on a monitor, thereby quickly detecting the handmade explosive in the bottle or the handmade explosive adhering to the surface of the bottle at a low erroneous alarm frequency.

14 Claims, 13 Drawing Sheets

FIG. 3

| | Detection target explosive components | Positive/Negative ion | m/z of ion (MS, MSMS) | Range of m/z | Threshold values (Count) | Relation with other component ions | Relation with other contamination ions |
|---|---|---|---|---|---|---|---|
| 1 | A | Positive | mA1(MS) | +0.5-0.5 | $1 \times 10^7$ | OR with 2 | NOT with M |
| 2 | A | Positive | mA2(MS) | +0.5-0.5 | $2 \times 10^8$ | OR with 1 | |
| 3 | B | Positive | mB1(MS) | +0.3-0.3 | $2 \times 10^6$ | AND with 4, 5 | NOT with M |
| 4 | B | Negative | mB2(MS) | +0.8-0.5 | $5 \times 10^6$ | AND with 3, 5 | |
| 5 | B | Negative | mB3(MSMS) | +0.3-0.3 | $3 \times 10^6$ | AND with 3, 4 | |
| 6 | C | Negative | mC1(MSMS) | +0.5-0.5 | $1 \times 10^7$ | | |
| ---- | ---- | ---- | ---- | ---- | ---- | ---- | ---- |
| M | Contamination component A | Negative | mKA1(MS) | +0.5-0.5 | $1 \times 10^7$ | | |

DANGEROUS SUBSTANCE DETECTION SYSTEM

CLAIM OF PRIORITY

The present application claims priority from Japanese patent application JP 2009-238438 filed on Oct. 15, 2009, the content of which is hereby incorporated by reference into this application.

BACKGROUND OF THE INVENTION

1. Field of the Invention

The present invention relates to security techniques for preventing terrorism and crimes using explosives.

2. Background Art

The threats of terrorism are increasing worldwide. Recently, production methods of explosives using daily commodities have been widely known, and terrorism and crimes using explosives have become threats in daily lives. In London, synchronized terrorist attacks targeting subways and buses occurred and caused many casualties. Moreover, according to press reports, also in Japan, incidents have occurred, for example, suspects who planned suicide terrorism in commuter trains were arrested.

In order to prevent terrorism and crimes, dangerous substance probing techniques are developed in various countries. For example, in JP2000-28579A, an explosive probing system using a mass spectrometer is described. The vapor leaked from baggage is collected by a sampling probe, and it is ionized by using a negative corona discharge and subjected to detection by using the mass spectrometer, thereby determining the presence or absence of dangerous substances.

In order to prevent dangerous liquid such as gasoline from being brought into, for example, an airplane, liquid detection systems have also been developed. For example, in JP2008-157685A, the weight and the permittivity of the bottle containing liquid are measured; and, if they deviate from reference values, it is determined to be a dangerous substance, and an alarm is activated.

SUMMARY OF THE INVENTION

The object of the conventional technique described in JP2000-28579A is mainly detection of military explosives and firing chemicals and industrial explosives, which are used in construction sites, etc. However, as a result of enhanced measures against terrorism in various countries, these military explosives and industrial explosives have put under stricter control. Therefore, except for war zones, it is difficult for criminals to obtain such explosives.

Therefore, recently, terrorism and crimes using handmade bombs have been particularly problematic. The handmade explosives used in the handmade bombs are synthesized by using daily commodities as raw materials, the production methods thereof are widely known through the Internet, and they tend to be used worldwide. Methods for quickly detecting these handmade explosives are required.

Also, regarding the handmade explosives, an attempted terrorism case, which was a plan to bring a liquid substance into an airplane and explode it during a flight, occurred. After this case, the liquid-like and gel-like substances in hand-carried baggage brought into airplanes were regulated. At present, detection of these liquid-like and gel-like substances needs determination by examiners using visual check and odors. However, it is difficult for the examiners to precisely distinguish the substances under the circumstance in which quick detection is required. Moreover, when the content of the bottle is replaced or sealed, the detection becomes difficult.

Therefore, like JP2008-157685A, liquid detection systems are also developed for preventing dangerous liquid such as gasoline from being brought into airplanes, etc. However, in this method, the type of the bottle and the weight of the content have to be read, the detection takes time correspondingly, and quick detection is difficult.

A conventional explosive probing machine such as that described in JP2000-28579A is mainly based on the presupposition of use in an airport or an important facility, and the object thereof is to check a comparatively small number of people. Upon usage in a mass transport system such as a station used by a massive number of passengers, two points, i.e., high throughput which enables check within a short period of time and reduction of the rate of erroneous alarms in which the probing machine reacts even when no explosive is owned, are important. Particularly, when the erroneous alarms occur, elaborate hand-carried baggage checks by examiners are required, which affects high throughput. Therefore, if the erroneous alarms occur, quick check is difficult.

The method for quickly detecting handmade explosives with a low erroneous alarm frequency is required for the above described reasons.

The present invention provides a dangerous substance detection system which quickly detects a dangerous substance in a bottle with a low erroneous alarm frequency. Even when the content of the bottle is replaced with a handmade explosive, a minute amount of the gas of the handmade explosive component is generated from a cap part thereof. The gas component can be specified by sucking-in the minute amount of gas and analyzing the gas by a highly-sensitive and highly-selective mass spectrometer. When a handmade explosive is handled, fine particles of the handmade explosive may adhere to the surface of the bottle. The gas component can also be specified by sucking-in a minute amount of the gas generated from the fine particles or sucking-in and gasifying the fine particles per se and subjecting the gas to mass spectroscopy.

An example of a dangerous substance detection system of the present invention includes: a bottle placement space for placing a bottle to be detected; an introduction region bored in the bottle placement space; an intake region for sucking-in a sample gas from the introduction region; an ion source for ionizing the sucked-in sample gas; a mass analysis region for subjecting an ion generated by the ion source to mass analysis; a data processor for controlling the ion source and the mass analysis region; a database region for retaining mass spectrum data derived from a handmade explosive; an identification region for collating the result of the mass analysis of the sample gas carried out by the mass analysis region with the mass spectrum data retained in the database region and determining presence/absence of the handmade explosive; and a monitor for displaying the result of the determination carried out by the identification region.

According to the present invention, highly precise detection of the substance in a bottle is facilitated, and, as a result, quick detection with a low false positive rate can be carried out. Therefore, not only hand-carried baggage detection in airports, but also detection in various events and customer-gathering facilities such as stations can be carried out; the risk of terrorism and crimes can be further reduced; and a contribution to building safe societies can be made.

BRIEF DESCRIPTION OF THE DRAWINGS

FIG. 3 is an explanatory drawing showing an example of a database.

DETAILED DESCRIPTION OF THE PREFERRED EMBODIMENTS

Hereinafter, embodiments of the present invention will be explained in detail by using drawings. Note that the system configurations and the contents of processing operations explained herein are examples of substantiation of the present invention, and modification examples implemented by combinations or replacements of them with known techniques are also included in the scope of the present invention.

(A) First Embodiment

Figure 1:
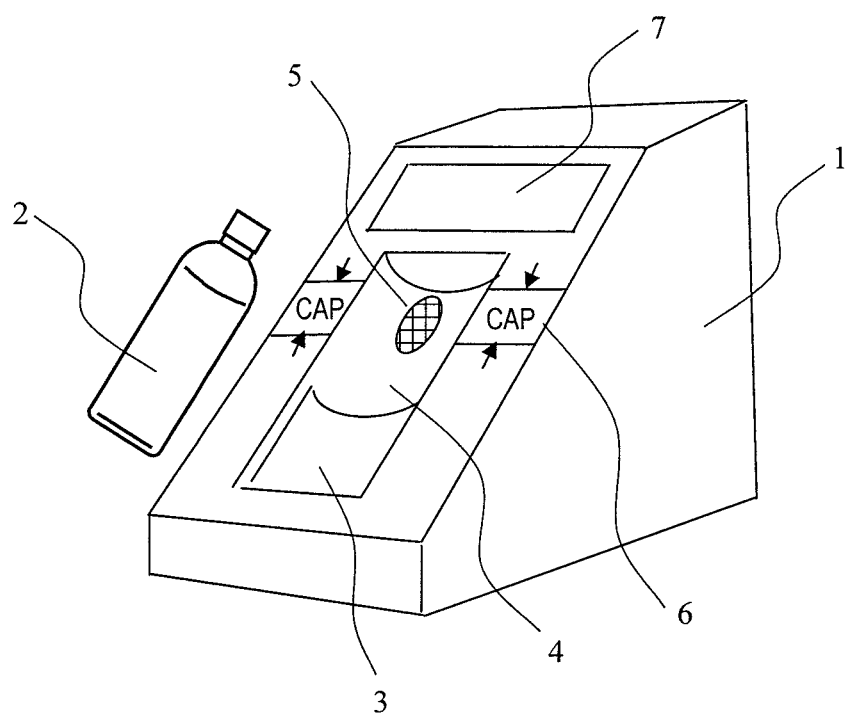
FIG. 1 is a schematic drawing showing an example of a detection system of the substance in a bottle according to the present invention.

Hereinafter, a first embodiment of the present invention will be explained. FIG. 1 is a schematic drawing showing an example of a detection system of the present embodiment of the substance in a bottle. A bottle placement space for placing the bottle 2 is provided on a front surface of the detection system 1. The bottle placement space includes a bottle placement space (big bottle) 3 for a big bottle. For example in the case of a PET (polyethylene terephthalate) bottle, the bottle placement space (big bottle) 3 presupposes a 500 mL bottle; however, the bottle placement space may be able to allow placement of a bottle larger than that. Moreover, the bottle placement space also includes a bottle placement space (small bottle) 4 for a small bottle and is structured so that a small bottle can also be placed thereon. For example in the case of a PET bottle, a 350 mL bottle is presupposed as the small bottle; however, the bottle placement space may be able to allow placement of a bottle smaller than that. The present embodiment presupposes two types of bottles, i.e., big bottles and small bottles; however, the bottle placement space may have a shape that allows placement of three or more types of bottles. Moreover, although PET bottles are taken as examples of bottles in the present embodiment, the detection system of the present invention can be applied to bottles made of aluminum or glass and the containers such as paper packages and plastic tubes which store liquids, gels, or solid substances. The detection system of the present invention is able to detect ultralow-volume gas components leaked from a cap part, seam, etc. of a bottle and fine particles adhering to the surface of the bottle.

As the manner of placing the bottle 2 onto the bottle placement space, the bottle may be placed so as to be horizontally laid or set upright; however, when the bottle placement space is structured so as to obliquely place the bottle, the bottle can be easily placed by hands, and the content of the bottle can be prevented from spilling. An introduction region 5, which sucks-in gases and fine particles of handmade explosive components in the bottle or adhering to the surface of the bottle, into the system is bored in the wall surface of the bottle placement space. The gases of the handmade explosives leaked from the cap part of the bottle 2, the gases from the fine particles of the handmade explosives adhering to the surface of the bottle, and the fine particles per se are sucked-in from the introduction region 5 into the system. FIG. 1 shows the case in which one introduction region 5 is provided; however, a plurality of introduction regions 5 may be provided. A cap marker 6 indicates the location to place the bottle so that the cap part of the bottle 2 is at the position of the introduction region 5. The positions and shapes of the bottle placement space (big bottle) 3 and the bottle placement space (small bottle) 4 are designed so that the cap of the bottle is positioned near the introduction region 5 when the bottle is placed on the bottle placement space both in the case of a large bottle and the case of a small bottle. In the case of the example shown in the drawing, the bottle placement space (small bottle) 4 is configured to be a recess provided to be deeper in the upper part of the placement surface of the bottle placement space (big bottle) 3.

The presence or absence of handmade explosive components is determined by analyzing a sample gas including the gases and the fine particles sucked-in from the introduction region 5, and the result thereof is displayed on a monitor 7. The time taken from placement of the bottle on the bottle placement space until display of the result is varied by the vapor pressure of a detection target substance. In the case of a handmade explosive having a comparatively high vapor pressure, the result can be shown in one second or less to several seconds or less. In the case of a substance having a low vapor pressure like military explosives, the result can be shown in several seconds or less to ten seconds or less.

In the present embodiment, analysis of the sample gas composed of the gases and fine particles sucked-in from the introduction region 5 is carried out; however, in combination, other methods such as spectroscopic analysis of the bottle content using near-infrared light and a method of analyzing the permittivity of liquid can also be carried out at the same time or individually.

Figure 2:
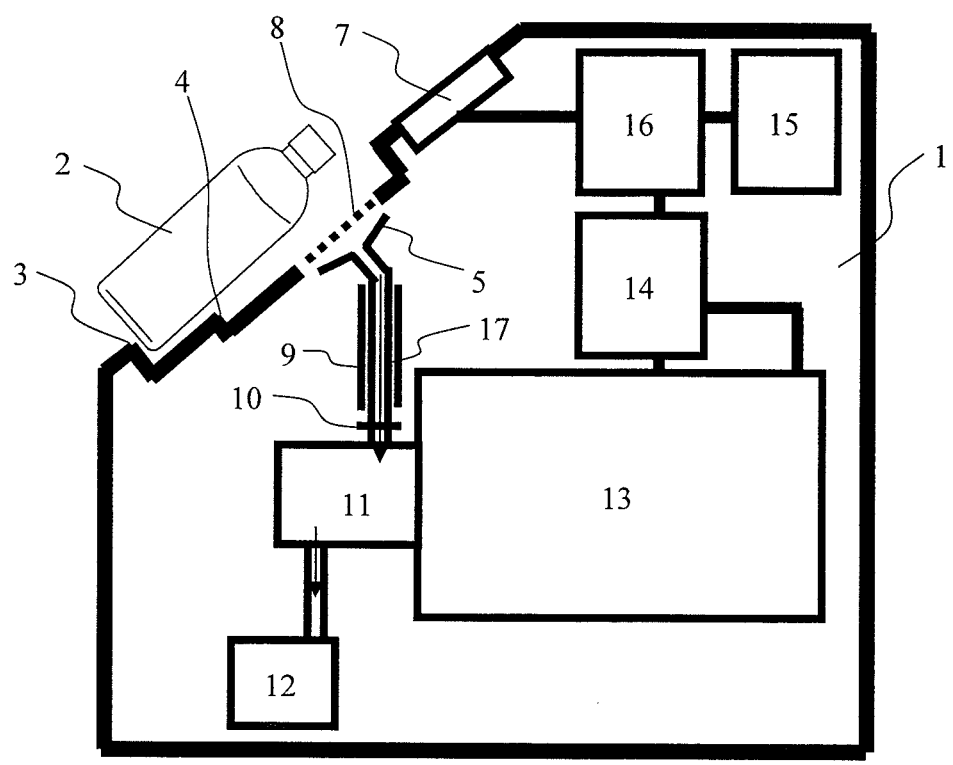
FIG. 2 is a drawing showing an example of the internal configuration of the detection system of the substance in the bottle according to the present invention.

FIG. 2 is a drawing showing an example of the internal configuration of the detection system of the present embodiment of the substance in the bottle. When the large bottle 2 is placed in the recess of the bottle placement space (big bottle) 3 of the detection system 1, the cap part of the bottle 2 is located at the position of the introduction region 5. On the other hand, in the case of a small bottle, when the bottle is placed in the recess of the bottle placement space (small bottle) 4, the cap part of the bottle 2 is similarly located at the position of the introduction region 5. In this manner, regardless of the size of the bottle, the cap part is configured to be located at the position of the introduction region 5. A rough mesh filter 8 is attached to the front surface of the introduction region 5 and prevents large dust from entering and fingers from entering the introduction region 5. For example, a metal-wire mesh (mesh size: 0.5 mm, opening rate: 50%) was used as the rough mesh filter 8. The rough mesh filter 8 is replaceable; and, when it is clogged with dust, the mesh is cleaned and reused or replaced with a new one.

The air near the cap of the bottle 2 including the gases and fine particles is sucked-in by an intake pump 12 from the introduction region 5 via a sample introduction pipe 17 and introduced into an ion source 11. The suction rate of the intake pump 12 is, for example, 2.0 L/min. At this suction rate, the air near the cap of the bottle can be introduced into the ion source in one second or less. The suction rate may be further increased or reduced. The sample introduction pipe 17 is heated by a pipe heater 9 and prevents the gases and the fine particles from adsorbing to the interior of the pipe. If a handmade explosive component is detected or if the introduction region 5 or the sample introduction pipe 17 is contaminated, it can be subjected to heating cleaning so that next detection can be carried out promptly. The pipe heater 9 can be heated to a maximum temperature of 300° C.; however, in the case of a handmade explosive, thermal decomposition due to the heating occurs; therefore, the pipe heater is desired to be used at 70 to 120° C., but may be used at 50° C. to 150° C. For example in the case of TATP (triacetone triperoxide), maximum detection sensitivity can be obtained by heating the sample introduction pipe 17 to 70° C.; however, detection of TATP can be carried out within a temperature range of 50° C. to 150° C. On the other hand, in the case of HMTD (hexamethylenetriperoxidediamine), maximum detection sensitivity can be obtained by heating the sample introduction pipe 17 to 120° C.; however, detection of HMTD can be carried out within a temperature range of 50° C. to 150° C. For example, when the sample introduction pipe 17 is heated to 150° C., TATP can be detected although the sensitivity thereof is lower than the maximum sensitivity; and, reversely, when the sample introduction pipe 17 is heated to 50° C., HMTD can also be detected. At an intermediate temperature, for example at 100° C., both of TATP and HMTD can be detected with the sensitivity of some level.

A fine mesh filter 10 is provided in the sample introduction pipe 17; as a result, the fine particles adhere to the fine mesh filter 10. Since the fine mesh filter 10 is heated by the pipe heater 9, the adhered fine particles are gasified and become a sample gas. The fine mesh filter 10 also has a role to prevent the ion source 11 from being contaminated with the dust failed to be collected by the rough mesh filter 8. For example, a 50 μmm stainless-steel-wire filter or a sintered-body filter can be used as the fine mesh filter 10. As well as the rough mesh filter 8, the fine mesh filter 10 can also be cleaned and reused or replaced with a new product in accordance with needs. The fine mesh filter 10 may be individually heated for gasifying the fine particles.

The ion source 11 can be an atmospheric-pressure chemical ionization source using negative corona discharge or positive corona discharge described, for example, in the publication of JP2000-28579A. The generation method of ions may be another method such as irradiation by a radiation source; irradiation of electrons, light, or laser light; penning discharge; or electrospray. The ions generated by the ion source 11 from the sample gas are subjected to mass analysis by a mass analysis region 13. For example, a wire-type linear ion trap mass spectrometer can be used as the mass analysis region 13. The method of mass analysis may be another method such as a linear ion trap mass spectrometer, a quadrupole ion trap mass spectrometer, a quadrupole filter mass spectrometer, a triple quadrupole mass spectrometer, a time-of-flight mass spectrometer, a magnetic-field mass spectrometer, or ion mobility. A signal measured by the mass analysis region 13 is measured as a mass spectrum by a data processor 14. Peaks of the mass number specific to handmade explosives are extracted from the mass spectrum. A database region 15 retains the information including average mass analysis data necessary for identifying handmade explosive substances. The retained information includes the values of mass/charge ratio (m/z), which is the mass number m of an ion divided by the valence z of the ion, and includes relative intensities. The mass spectrum measured by the mass analysis region 13 is transmitted to an identification region 16 and subjected to data processing such as collation with the data of the handmade explosives read from the database region 15, thereby specifying the handmade explosive substances.

FIG. 3 is an explanatory drawing showing an example of the information retained by the database 15. The database 15 stores information such as: component substances of handmade explosives which are detection targets, the classification of whether it is positive ion detection or negative ion detection, the classification of whether it is mass analysis (MS) or tandem analysis (MSMS), mass/charge ratios of the ions derived from the handmade explosive components, the ranges of the mass/charge ratios, threshold values for determining detection, and whether AND or OR with the ions derived from other handmade explosive components is to be obtained or whether NOT with the ions derived from contamination components is to be obtained. The presence/absence of the specified handmade explosive substances and/or the result of the mass analysis is shown on the monitor 7. For example when the handmade explosive component is detected, the monitor 7 lights a red lamp; when no handmade explosive component is detected, the monitor lights a blue lamp; and, in the case of the vicinity of the threshold value, the monitor lights a yellow lamp. The display method of the result is not limited to lighting of the lamps, as long as the operator thereof can recognize the presence/absence of detection, for example, by changing the display state of the entire or part of the screen of the monitor 7. Instead of visual display, alarming by the sound of, for example, a buzzer may be carried out. Alternatively, the detected matter can be displayed by characters or colors. Alternatively, the intensities of the detected ions may be displayed on the screen by a bar graph, numbers, etc.

Figure 4:
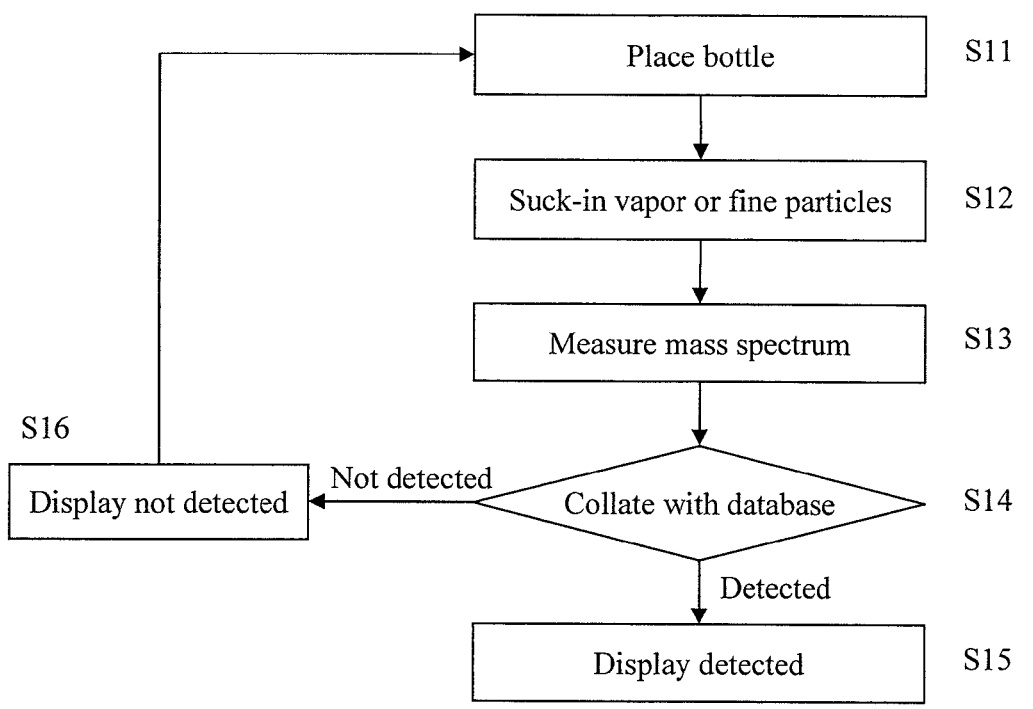
FIG. 4 is a drawing showing an example of the processing procedure of handmade explosive detection according to the present invention.

FIG. 4 is a drawing showing an example of the processing procedure of the handmade explosive detection according to the present invention. The bottle, which is a detection object, is placed on the bottle placement space of the detection system (S11), vapor or fine particles are sucked-in manually or automatically by the intake pump (S12). The vapor or the fine particles are subjected to mass analysis so as to measure a mass spectrum (S13). The measured mass spectrum is collated with the database, thereby displaying the presence/absence of a handmade explosive and/or the result of the mass analysis (S15, S16).

Figure 5:
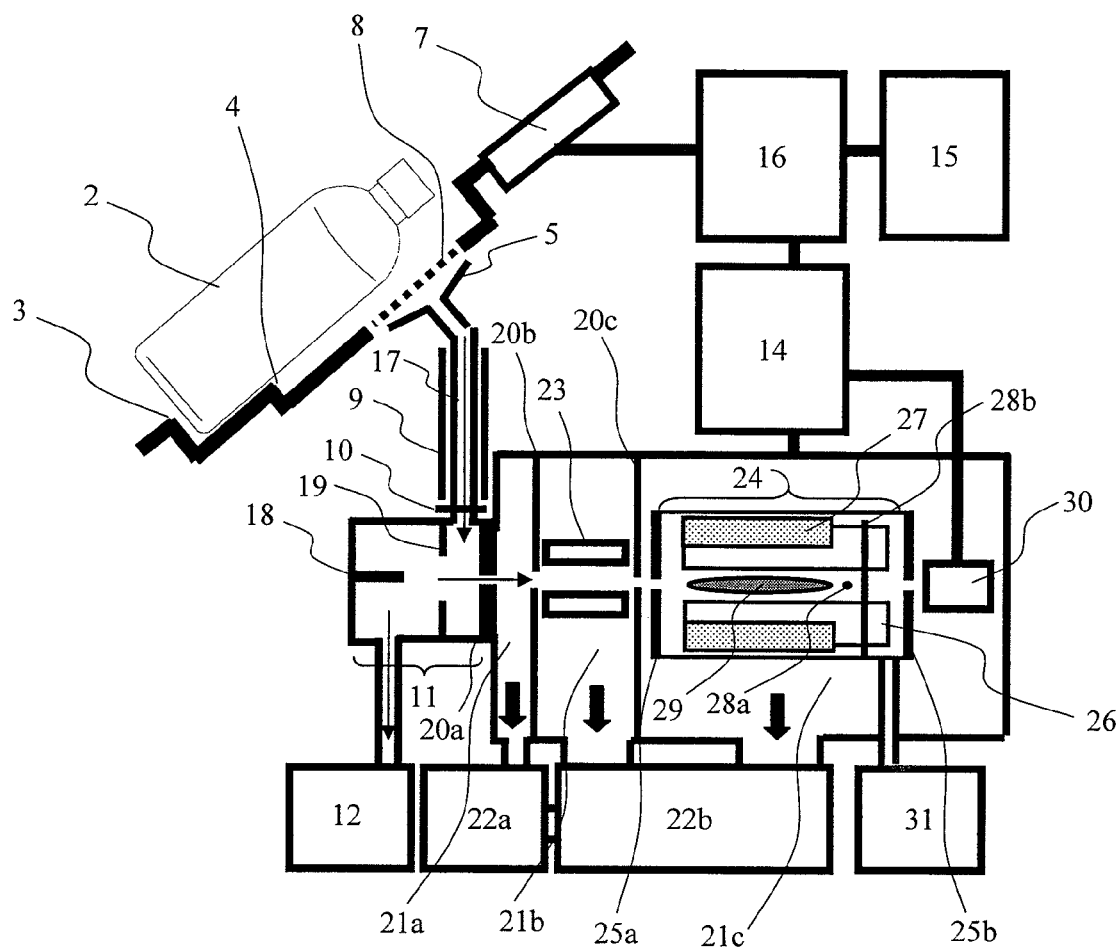
FIG. 5 is a drawing showing an example of a mass analysis region.

FIG. 5 is a drawing showing an example of the mass analysis region of the present embodiment. Herein, an example in which the wire-type linear ion trap mass spectrometer is used as the mass analysis region will be explained. In the ion source 11, primary ions are generated by a corona discharge in the atmosphere, and the sample gas is ionized by utilizing the chemical reactions between the primary ions and the sample gas. A needle electrode 18 is disposed in the ion source 11, a high voltage is applied between the electrode and a counter electrode 19, and a corona discharge is generated near the distal end of the needle electrode 18. For example, in positive ionization, a voltage of 5 kV was applied; and, in negative ionization, a voltage of −4 kV was applied. The nitrogen, oxygen, water vapor, etc. in air are ionized by the corona discharge and become primary ions. The generated primary ions are moved to a first aperture 20a side by an electric field. The sample gas sucked-in via the sample introduction pipe 17 flows to the needle electrode 18 side through the opening of the counter electrode 19. Then, the sample gas is reacted with the primary ions, thereby ionizing the sample gas.

The ions of the ionized sample gas are introduced into an ion trap region 24 of a vacuum region 21c via a first aperture 20a, a first differential pumping region 21a, a second aperture 20b, a second differential pumping region 21b, and a third aperture 20c. Differential pumping is carried out for introducing the ions from the atmosphere to vacuum. A vacuum pump 22a and a vacuum pump 22b were used in the differential pumping. The single vacuum pump 22b is able to carry out vacuum pumping at two locations. The vacuum pump 22a was also used as a roughing pump of the vacuum pump 22b. The method of the differential pumping may be a different method, for example, individual usage of vacuum pumps. Regarding the hole diameter of each aperture, for example, the aperture of the first aperture 20a has an inner diameter of 0.12 mm, a length of 10 mm, the aperture of the second aperture 20b has an inner diameter of 0.5 mm, and the aperture of the third aperture 20c has an inner diameter of 1.2 mm. The hole diameter of the apertures depends on the emission volume of the vacuum pumps. The second differential pumping region 21b is provided with an ion guide 23. Instead of the ion guide, for example, an ion lens may be used. Also, the first differential pumping region 21a, the second differential pumping region 21b, and the vacuum region 21c may be provided with, for example, ion guides or ion lenses. The ion source 11, the first aperture 20a, and the second aperture 20b are desired to be heated in order to prevent contaminants, etc. from adhering to the interior thereof.

The ion trap region 24 is composed of an inlet end lens 25a, an outlet end lens 25b, quadrupole rods 26, excitation electrodes 27 inserted between the gaps of the quadrupole rods 26, a trap wire 28a, and an extraction wire 28b. A buffer gas necessary for ion trapping and ion dissociation is supplied to the ion trap region 24 from a gas supply unit 31. A helium gas was used in the present embodiment; however, the gas may be air, argon, nitrogen, etc. The ions introduced into the ion trap region 24 are trapped by a trap region 29 shown in the figure by the electrostatic potential in the axial direction between the inlet end lens 25a and the trap wire 28a and the quadrupole potential of the quadrupole rods 26 in the radial direction. When an AC voltage is applied to the excitation electrodes 27 inserted between the quadrupole rods 26, only the ions of particular m/z are resonantly excited in the direction of the excitation electrodes 27 and discharged in the axial direction by the extraction electric field formed by the extraction wire 28b. The ions of the particular m/z are detected by a detector 30. A mass spectrum can be obtained by controlling the resonance conditions and the voltages of the electrodes by the data processor 14 and discharging the ions of arbitrary m/z.

One time of the measurement of the mass spectrum can be carried out, for example, in 100 milliseconds. Moreover, positive ions and negative ions can be alternately measured. Specifically, for example, positive ions are measured in 0.5 second; then, the electrodes are switched at a high speed for negative ion detection, thereby measuring negative ions in 0.5 second; and the electrodes are switched again at a high speed for positive ion detection, thereby measuring positive ions. By repeating this, the mass spectrum of the positive ions and the mass spectrum of the negative ions are measured. As a result, the mass spectrums of both the positive and negative ions can be measured in one second. The switching speed can be further increased. Upon measurement of the positive ions (or negative ions), mass spectrums having different mass ranges, and a plurality of spectrums such as normal mass spectrums and tandem mass spectrums can also be measured. The switching of the measurement mode and the continuous measurement are carried out under the control of the data processor 14. The measured mass spectrums are transmitted to the identification region 16 and subjected to data processing such as collation with the information of the database of the handmade explosives read from the database region 15, and specification of the handmade explosive substances is carried out. The presence/absence of the specified handmade explosive substances and/or the result of mass analysis are displayed on the monitor 7. In the present embodiment, the wire-type linear ion trap mass spectrometer was used in the mass analysis region; however, a different mass analysis method, wherein for example, a quadrupole ion trap, a quadrupole filter, or ion mobility serves as the ion trap region 24, may be employed.

Figure 6:
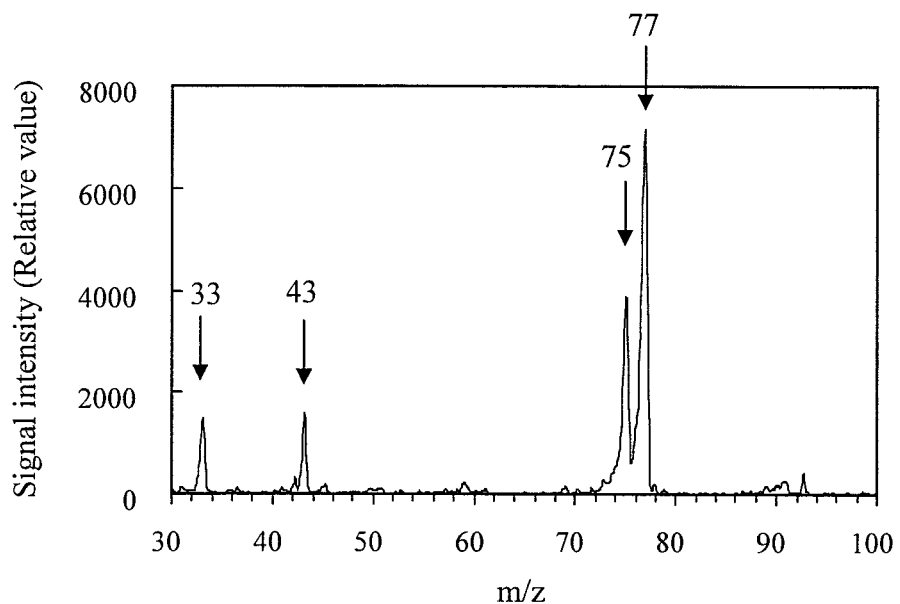
FIG. 6 is a drawing showing an example of the mass spectrum of triacetone triperoxide measured by the detection system of the present invention.

A typical substance which is a component of handmade explosives was measured by the detection system of the present invention. FIG. 6 is a drawing showing an example of the mass spectrum of triacetone triperoxide measured by the detection system of the present invention. Several micrograms of triacetone triperoxide fine particles were caused to adhere to the vicinity of the cap of a bottle, and the bottle was set in the detection system of the present invention. In positive ion detection, the introduction region and the sample introduction pipe were heated to 70° C., and the ion source and the first aperture were heated to 120° C. Signals of m/z=33, 43, 75, and 77 were detected. The molecular weight (M) of triacetone triperoxide is 222. The peak m/z=75 is estimated to be $(M/3+H)^+$. The other peaks m/z=33, 43, and 77 are the signals of the decomposed matters of triacetone triperoxide. Therefore, when at least one signal among those of m/z=33, 43, 75, and 77 is detected, triacetone triperoxide is considered to have been detected. If triacetone triperoxide is considered to have been detected when a plurality of peaks among the peaks m/z=33, 43, 75, and 77 are detected, there is an advantage that the frequency of erroneous alarms is lowered. For example, in the case in which detection is determined only by the peak of m/z=77, an erroneous alarm occurs if a different component is coincidentally detected at the peak of m/z=77. However, when triacetone triperoxide is considered to have been detected in the case in which at least one of the other peaks of m/z=33, 43, and 75 is detected at the same time, the possibility of an erroneous alarm can be reduced.

Figure 7:
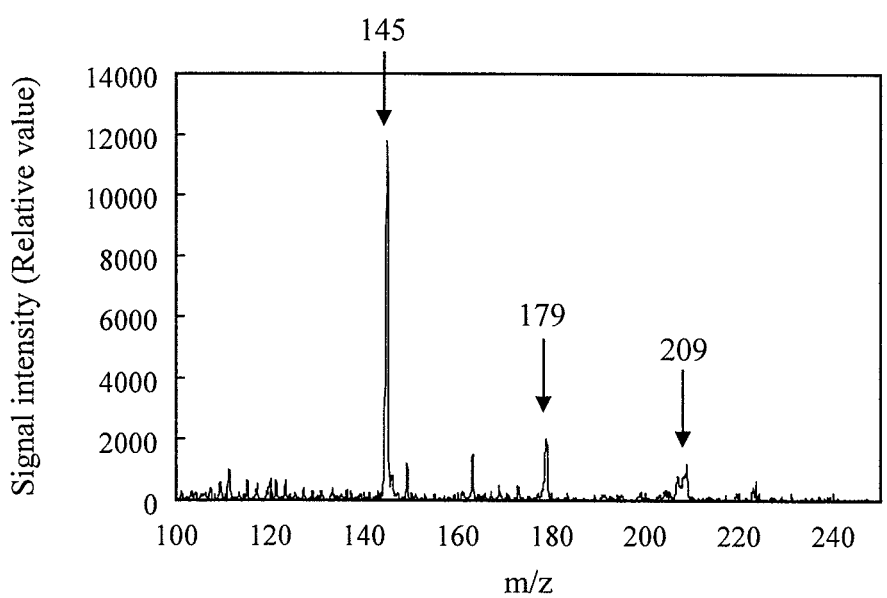
FIG. 7 is a drawing showing an example of the mass spectrum of hexamethylenetriperoxidediamine measured by the detection system of the present invention.

FIG. 7 is a drawing showing an example of the mass spectrum of hexamethylenetriperoxidediamine measured by the detection system of the present invention. Several micrograms of hexamethylenetriperoxidediamine fine particles were caused to adhere to the vicinity of the cap of a bottle, and the bottle was set in the detection system of the present invention. In positive ion detection, the introduction region and the sample introduction pipe were heated to 100° C., and the ion source and the first aperture were heated to 120° C. Signals of m/z=145, 179, and 209 were detected. The molecular weight (M) of hexamethylenetriperoxidediamine is 208. The peak m/z=209 is estimated to be $(M+H)^+$. The other peaks m/z=145 and 179 are the signals of the decomposed matters of hexamethylenetriperoxidediamine. Therefore, when at least one signal among those of m/z=145, 179, and 209 is detected, hexamethylenetriperoxidediamine is considered to have been detected. If hexamethylenetriperoxidediamine is considered to have been detected when a plurality of peaks among the peaks m/z=145, 179, and 209 are detected, there is an advantage that the frequency of erroneous alarms is lowered. For example, in the case in which detection is determined only by the peak of m/z=145, an erroneous alarm occurs if a different component is coincidentally detected at the peak of m/z=145. However, when hexamethylenetriperoxidediamine is considered to have been detected in the case in which at least one of the other peaks of m/z=179 and 209 is detected at the same time, the possibility of an erroneous alarm can be reduced.

Figure 8:
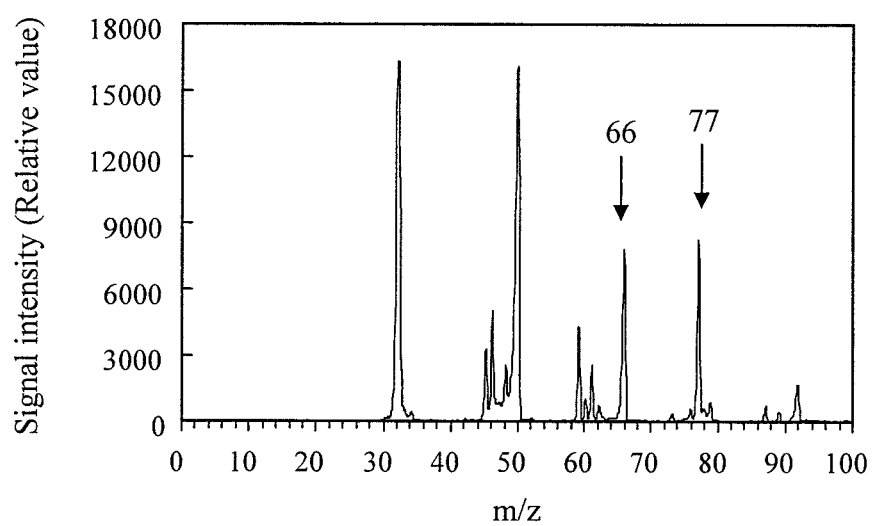
FIG. 8 is a drawing showing an example of the mass spectrum of hydrogen peroxide obtained by the detection system of the present invention.

FIG. 8 is a drawing showing an example of the mass spectrum of hydrogen peroxide, which is a raw material of a handmade explosive, obtained by the detection system of the present invention. Hydrogen peroxide of a 30% aqueous solution was used as a sample. About 100 mL of hydrogen peroxide was put into a bottle, the cap thereof was closed, and the bottle was set in the detection system of the present invention. In negative ion detection, the introduction region and the sample introduction pipe were heated to 70° C., and the ion source and the first aperture were heated to 120° C. Signals of m/z=66 and 77 were detected. The molecular weight (M) of hydrogen peroxide is 34. The peak m/z=66 is estimated to be $(M+O_2)^-$, and the peak m/z=77 is estimated to be $(CO_3OH)^-$. Therefore, when at least one signal among those of m/z=66 and 77 is detected, hydrogen peroxide is considered to have been detected. If hydrogen peroxide is considered to have been detected when a plurality of peaks among the peaks m/z=66 and 77 are detected, there is an advantage that the frequency of erroneous alarms is lowered. For example, in the case in which detection is determined only by the peak of m/z=66, an erroneous alarm occurs if a different component is coincidentally detected at the peak of m/z=66. However, when hydrogen peroxide is considered to have been detected in the case in which the other peak of m/z=77 is detected at the same time, the possibility of an erroneous alarm can be reduced.

(B) Second Embodiment

Hereinafter, a second embodiment of the present invention will be explained. In the present embodiment, tandem mass analysis is carried out with respect to the ion peaks derived from detected handmade explosive components, and dissociated unique fragment ions serve as detection targets. The concentration of the substances leaked from the interior of the bottle is extremely low; therefore, the system for detection is required to have extremely high sensitivity. When the tandem mass analysis is carried out, background is reduced; therefore, highly-sensitive measurement can be carried out, and this is particularly effective to detection of the matters leaked from the interior of the bottle as shown in the present embodiment.

A tandem mass analysis method is known as a method for enhancing selectivity in a mass spectrometer. Examples of a system for carrying out the tandem mass analysis method include: a linear ion trap mass spectrometer, a quadrupole ion trap mass spectrometer, and a triple quadrupole mass spectrometer. In the tandem mass analysis method, mass analysis is carried out by two stages. As the mass analysis of the first stage, the ratios m/z of the ions generated by the ion source are measured. The ions having particular ratios m/z are selected (isolation) from among the ions having various ratios m/z. Next, the selected ions (precursor ions) are dissociated by collision with, for example, a neutral gas, thereby generating decomposed-matter ions (fragment ions). Then, as the mass analysis of the second stage, mass analysis of the fragment ions is carried out. Upon dissociation of the precursor ions, which part in the molecules thereof is to be detached depends on the strength of the chemical bonds thereof. Therefore, when the fragment ions are analyzed, a mass spectrum including the information of the molecular structure of the precursor ions can be obtained. Therefore, even when, among the ions generated by the ion source, the ions of the ratios m/z of the contamination components and the ions of the particular ratios m/z of the handmade explosive component, which is a detection target, coincidentally have the same ratio m/z of the ions, whether the handmade explosive component is contained or not can be determined by checking the mass spectrum of the fragment ions.

Since the tandem mass analysis method using the linear ion trap mass spectrometer, the quadrupole ion trap mass spectrometer, or the triple quadrupole mass spectrometer is widely known, detailed explanations thereof will be omitted. In addition to the effects of improving the selectivity and preventing erroneous detection, the tandem mass analysis method is extremely effective also for detection of an ultralow amount of gas components. Specifically, the precursor ions are dissociated, and the fragment ions are detected; therefore, the dissociation has the effect of reducing background noise such as chemical noise. Therefore, even the ultralow amount of components which are mixed in the background noise and cannot be detected in normal mass analysis can be detected since the background noise is reduced.

An example of the tandem mass analysis using the wire-type linear ion trap mass spectrometer used in the present embodiment will be explained by FIG. 5. The ions introduced into the ion trap region 24 are trapped in the trap region 29 shown in the figure by the electrostatic potential in the axial direction between the inlet end lens 25a and the trap wire 28a and the quadrupole potential of the quadrupole rods 26 in the radial direction. An AC voltage is applied to the excitation electrodes 27 inserted between the quadrupole rods 26, and the matters except for the precursor ions of particular m/z desired to remain are resonantly excited in the direction of the excitation electrodes 27 and removed (isolation). At this point, the ions of a plurality of particular ratios m/z may remain. With respect to the remaining precursor ions of the particular ratio m/z, an AC voltage is applied to the excitation electrodes 27 inserted between the quadrupole rods 26, thereby exciting the ions and causing the ions to collide with the neutral gas (for example, helium gas) supplied into the ion trap. The energy of the excitation herein is the energy at the level that does not remove the ions to the outside from the inside of the ion trap. The precursor ions of the particular ratio m/z collided with the neutral gas are dissociated, and fragment ions thereof are generated and trapped in the ion trap. An AC voltage is applied to the excitation electrodes 27 inserted between the quadrupole rods 26, thereby discharging the fragment ions in the axial direction by an extraction electric field formed by the extraction wire 28b. The fragment ions of the particular ratio m/z are detected by the detector 30.

When resonance conditions and the voltages of the electrodes are controlled by the data processor 14 so as to discharge the fragment ions of an arbitrary ratio m/z, the mass spectrum of the fragment ions can be obtained. The mass spectrum of the fragment ions is a mass spectrum including the information of the molecular structure of the precursor ions. The mass spectrum of the fragment ions is transmitted to the identification region 16 and subjected to data processing such as collation with the database of the handmade explosives read from the database region 15, and specification of a handmade explosive substance is carried out. The presence/absence of the specified handmade explosive substance and/or the result of the mass analysis are displayed on the monitor 7. Therefore, among the ions generated by the ion source, even when the ions of the ratios m/z of the contamination components and the ions of the specific ratio m/z of the handmade explosive component, which is a detection target, coincidentally have the same ratio m/z of ions, whether the handmade explosive component is contained in the sucked-in sample or not can be determined by checking the mass spectrum of the fragment ions.

Figure 9A:
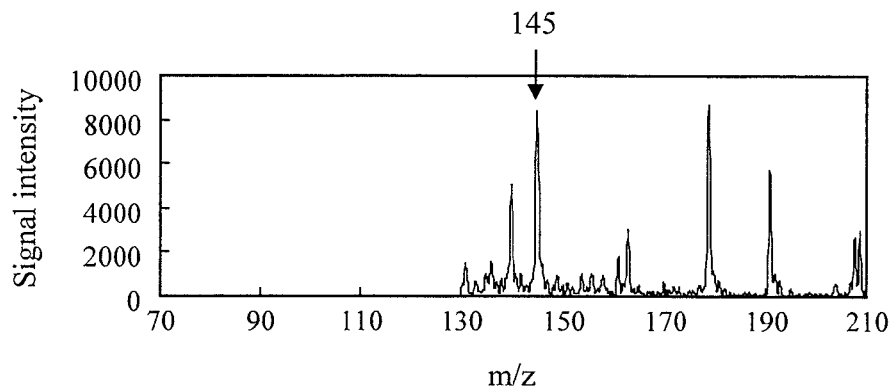
FIGS. 9A to 9C are drawings showing an example of a mass spectrum obtained by subjecting hexamethylenetriperoxidediamine to tandem mass analysis by the detection system of the present invention.
Figure 9B:
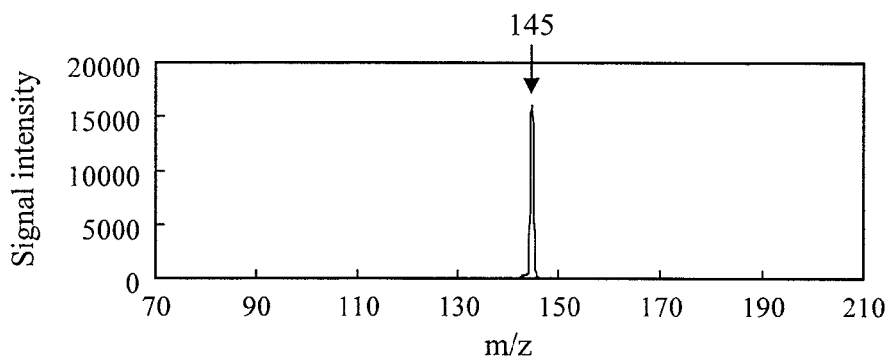
Figure 9C:
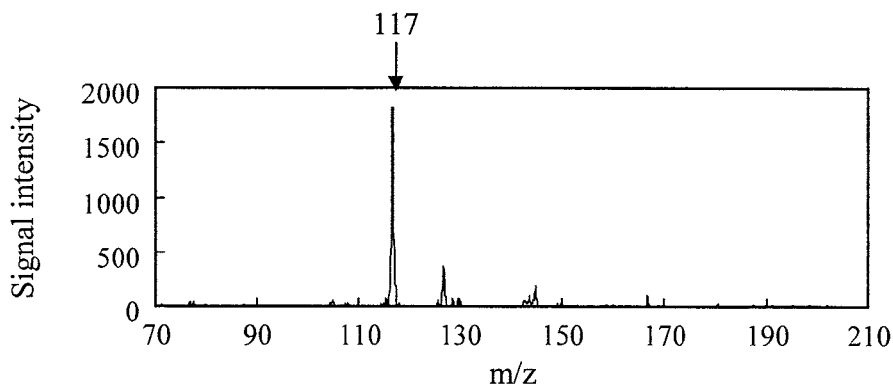

An example of detecting a handmade explosive by the tandem mass analysis will be explained in detail. FIGS. 9A to 9C are drawings showing an example of the mass spectrum obtained by subjecting hexamethylenetriperoxidediamine to the tandem mass analysis by the detection system of the present invention. FIG. 9A shows the mass spectrum obtained by the mass analysis of the first stage. The peak m/z=145 of this mass spectrum is a signal of a decomposed matter of hexamethylenetriperoxidediamine and is a mass peak derived from a handmade explosive. The ions of the peaks m/z other than this peak are considered to be the signals derived from contamination components. FIG. 9B shows a mass spectrum after the isolation, wherein the precursor ions are selectively ion-trapped. The ions except for the ions of m/z=145 which are the ions derived from the handmade explosive are resonantly excited by the excitation electrodes 27 and removed. In other words, the peak m/z=145 represents the precursor ions which are the ions derived from the handmade explosive. Next, the ions of m/z=145 (precursor ions) which are the ions derived from the handmade explosive are dissociated by collision with, for example, a neutral gas, thereby generating decomposed-matter ions (fragment ions). FIG. 9C shows a mass spectrum of the fragment ions obtained by dissociating the precursor ions of m/z=145 which are the ions derived from the handmade explosive. The signal of m/z=117 was detected as the fragment ions. The peak m/z=117 is a signal of the fragment ions which are the decomposed matters of hexamethylenetriperoxidediamine. Therefore, when the precursor ions of m/z=145 are dissociated and the fragment ions of m/z=117 are detected, it can be determined that hexamethylenetriperoxidediamine, which is a handmade explosive, has been detected. In the tandem mass analysis, sensitivity and precision can be improved by 10 times or more that of normal mass analysis.

When triacetone triperoxide is subjected to tandem mass analysis, for example, the ions of m/z=75 were selected as precursor ions, and the ions except for the ions of m/z=75 were resonantly excited and removed. The ions (precursor ions) of m/z=75 are dissociated by collision with, for example, a neutral gas, thereby generating decomposed-matter ions (fragment ions). The signal of m/z=48 was detected as the fragment ions. The peak m/z=48 is a signal of the fragment ions which are the decomposed matters of triacetone triperoxide. Therefore, when the precursor ions of m/z=75 are dissociated and the fragment ions of m/z=48 are detected, it can be determined that triacetone triperoxide, which is a handmade explosive, has been detected.

Figure 10A:
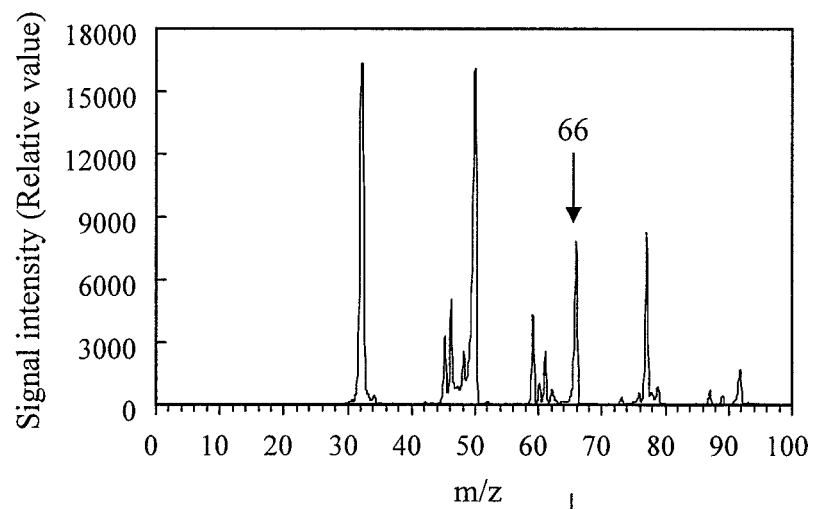
FIGS. 10A and 10B are drawings showing an example of the mass spectrum obtained by subjecting the ions of m/z=66 of hydrogen peroxide to the tandem mass analysis by the detection system of the present invention.
Figure 10B:
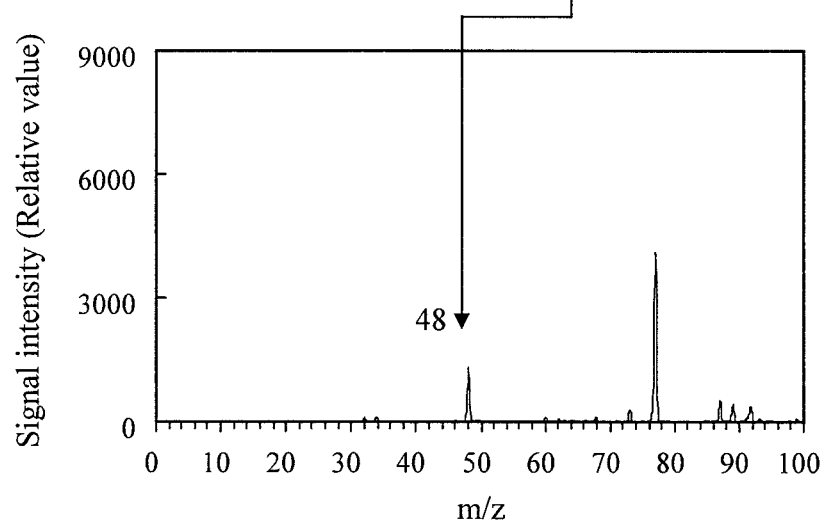

FIGS. 10A and 10B are drawings showing an example of the mass spectrum obtained by subjecting the ions of m/z=66 of hydrogen peroxide, which is a handmade explosive, to the tandem mass analysis by the detection system of the present invention. FIG. 10A shows a mass spectrum obtained by carrying out the mass analysis of the first stage. The peak m/z=66 of this mass spectrum is the mass peak derived from hydrogen peroxide, which is the handmade explosive. The peak m/z=66 is estimated to be $(M+O_2)^-$. The ions of m/z=66 were selected as precursor ions, and the ions except for the ions of m/z=66 were resonantly excited and removed. The ions (precursor ions) of m/z=66 are dissociated by collision with, for example, a neutral gas, thereby generating decomposed-matter ions (fragment ions). FIG. 10B shows a mass spectrum of the fragment ions obtained by dissociating the precursor ions of m/z=66, which are the ions derived from the handmade explosive. The signal of m/z=48 was detected as the fragment ions. The peak m/z=48 is a signal of the fragment ions which are the decomposed matters of hydrogen peroxide. Therefore, when the precursor ions of m/z=66 are dissociated and the fragment ions of m/z=48 are detected, it can be determined that hydrogen peroxide, which is a handmade explosive, has been detected.

Figure 11A:
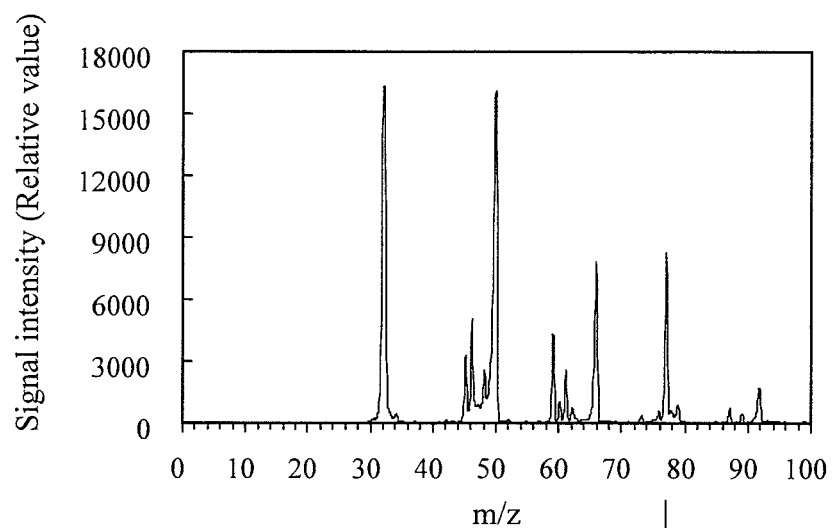
FIGS. 11A and 11B are drawings showing an example of the mass spectrum obtained by subjecting the ions of m/z=77 of hydrogen peroxide to the tandem mass analysis by the detection system of the present invention.
Figure 11B:
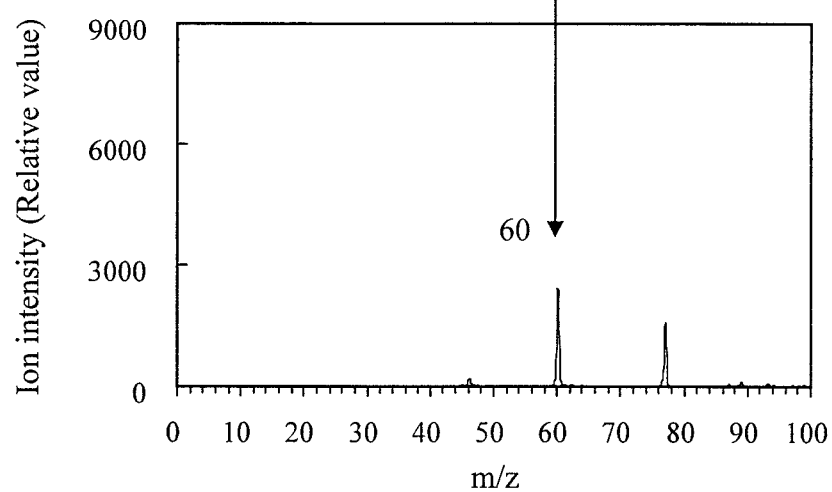

An example in which different precursor ions of hydrogen peroxide, which is a handmade explosive, is subjected to the tandem mass analysis will be explained. FIGS. 11A and 11B are drawings showing an example of the mass spectrum obtained by subjecting the ions of m/z=77 of hydrogen peroxide to the tandem mass analysis by the detection system of the present invention. FIG. 11A shows a mass spectrum obtained by carrying out the mass analysis of the first stage. The peak m/z=77 of this mass spectrum is the mass peak derived from hydrogen peroxide, which is the handmade explosive. The peak m/z=77 is estimated to be $(CO_3OH)^-$. The ions of m/z=77 were selected as precursor ions, and the ions except for the ions of m/z=77 were resonantly excited and removed. The ions (precursor ions) of m/z=77 are dissociated by collision with, for example, a neutral gas, thereby generating decomposed-matter ions (fragment ions). FIG. 11B shows a mass spectrum of the fragment ions obtained by dissociating the precursor ions of m/z=77, which are the ions derived from the handmade explosive. The signal of m/z=60 was detected as the fragment ions. The peak m/z=60 is a signal of the fragment ions which are the decomposed matters of hydrogen peroxide. Therefore, when the precursor ions of m/z=77 are dissociated and the fragment ions of m/z=60 are detected, it can be determined that hydrogen peroxide, which is a handmade explosive, has been detected. In the case of hydrogen peroxide, which is a handmade explosive, either one of or both of m/z=66 and m/z=77 are subjected to the tandem mass analysis as precursor ions at the same time or either peak at a time; as a result, the probability of successful detection is increased, the selectivity is further improved, and erroneous detection can be prevented.

Figure 12:
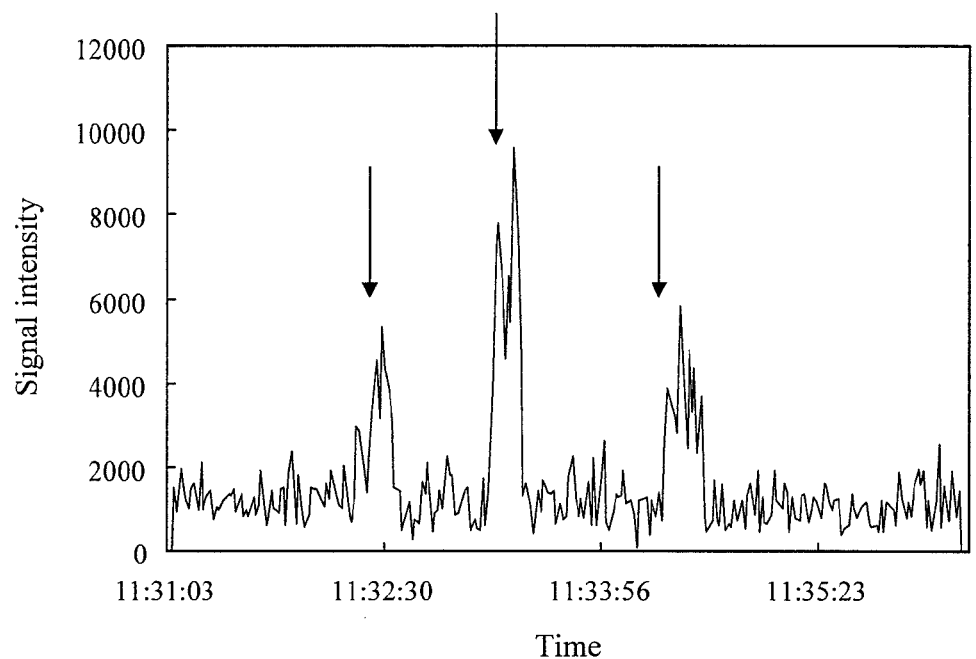
FIG. 12 is a drawing showing an example in which hydrogen peroxide in a bottle is detected by the tandem mass analysis by using the detection system of the present invention.

The tandem mass analysis method is extremely effective not only to the effects of improving the selectivity and preventing erroneous detection, but also to detection of ultralow amount of gas components. An example in which an ultralow amount of a handmade explosive was detected will be explained. FIG. 12 is a drawing showing an example in which a bottle filled with hydrogen peroxide and having a cap tightly closed was subjected to detection by the tandem mass analysis by using the detection system of the present invention. The ions of m/z=66 which was a mass peak derived from hydrogen peroxide serving as a handmade explosive were selected as precursor ions; the ions except for the ions of m/z=66 were resonantly excited and removed so as to dissociate m/z=66, and fragment ions of m/z=48 which were decomposed matters of hydrogen peroxide were detected. The arrows represent signal variation upon setting on the detection system. The detection was confirmed about in one second after setting in the detection system. The fragment ions of m/z=48 were reacted only when the bottle is set in the detection system, and the fragment ions derived from hydrogen peroxide, which was a handmade explosive, was reliably detected. When the fragment ions are detected, an alarm is emitted.

Without opening a cap of a PET bottle, the content thereof was replaced with hydrogen peroxide, which was a handmade explosive; and an example in this case will be explained, wherein a gas component of hydrogen peroxide, which was an ultralow amount of handmade explosive, was detected from the part of the unopened cap. Without opening the cap of the bottle, a hole was made therein by an injector, the content thereof was removed, and hydrogen peroxide, which was the handmade explosive, was injected thereinto by the injector. Then, the hole of the injector was sealed by an adhesive agent. In this case, the cap is not opened; therefore, it is unopened in appearance; however, the content has been replaced. The gas component of hydrogen peroxide, which is the handmade explosive, slightly leaked from the cap part has to be detected.

Figure 13:
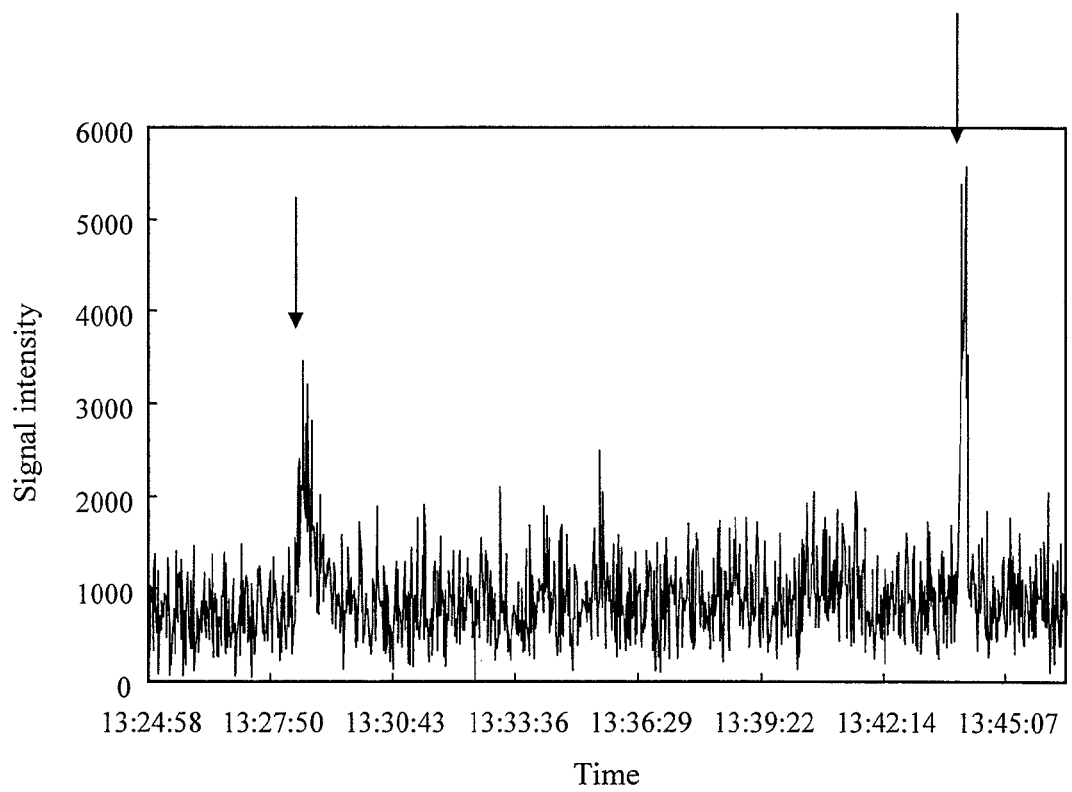
FIG. 13 is a drawing showing an example in which hydrogen peroxide in a bottle is detected by the tandem mass analysis by using the detection system of the present invention.

FIG. 13 is a drawing showing an example in which hydrogen peroxide replacing the content of an unopened bottle by an injector was subjected to detection by the tandem mass analysis by using the detection system of the present invention. The ions of m/z=66 which was a mass peak derived from hydrogen peroxide serving as a handmade explosive were selected as precursor ions; the ions except for the ions of m/z=66 were resonantly excited and removed so as to dissociate m/z=66, and fragment ions of m/z=48 which were decomposed matters of hydrogen peroxide were detected. The arrows represent signal variation upon setting on the detection system. The detection was confirmed about in one second after setting in the detection system. The fragment ions of m/z=48 were reacted only when the bottle is set in the detection system, and the fragment ions derived from hydrogen peroxide, which was a handmade explosive, was reliably detected. When the fragment ions are detected, an alarm is emitted.

(C) Third Embodiment

Figure 14:
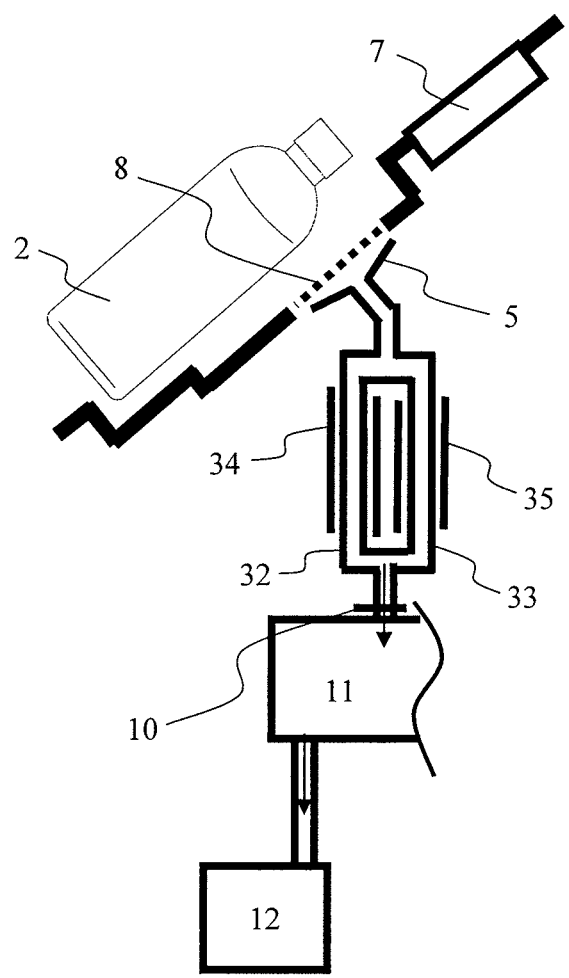
FIG. 14 is a drawing showing an example of a plurality of sample introduction pipes provided in the detection system.

An example of the detection system of the present invention using a plurality of sample introduction pipes and controlling the temperatures of the sample introduction pipes will be explained. FIG. 14 is a drawing showing an example of the plurality of sample introduction pipes provided in the detection system. The fine mesh filter 10, the ion source 11, and subsequent parts such as the mass analysis region are the same as those of the first embodiment and the second embodiment. The gas and fine particles contained in the air near the cap of the bottle are sucked-in by the intake pump 12 from the introduction region 5 and introduced into the ion source 11 via the sample introduction pipes 32 and 33. The sample introduction pipe 32 is heated by a pipe heater 34, and the sample introduction pipe 33 is heated by a pipe heater 35. The temperatures of the pipes can be changed in accordance with the characteristics of the gas and the fine particles to be detected. For example, the heating temperature of the pipe heater 34 is set to 70° C., and the heating temperature of the pipe heater 35 is set to 120° C. The pipe heater 34 may be in the temperature range of 50° C. to 120° C., and the pipe heater 35 may be in the temperature range of 100° C. to 150° C. Although it is not shown in the figure, the introduction region 5 is heated to 70° C. by a heater.

The sample introduction pipe 32 is mainly used upon detection of the substances such as triacetone triperoxide and nitroglycerin, which are easily decomposed under a high vapor pressure. If the temperature is high, these substances may be thermally decomposed, wherein detection sensitivity cannot be obtained due to the characteristic. Therefore, the appropriate temperature of the sample introduction pipe with respect to triacetone triperoxide, nitroglycerin, and the like is 70° C. to 120° C. On the other hand, the sample introduction pipe 33 is mainly effective to the substances such as hexamethylenetriperoxidediamine, which is not easily thermally decomposed compared with above described triacetone triperoxide and adsorb onto the interior of the pipe when the vapor pressure is low and the pipe temperature is low. Thus, the sample introduction pipe 33 can prevent adsorption of explosive components onto the interior of the pipe by heating the pipe to 120° C. by the pipe heater 35. When it is 120° C. or more, low-vapor-pressure components such as military explosives can also be detected. Regarding triacetone triperoxide, the detection sensitivity is high when the pipe temperature is 70° C., and the detection sensitivity is lowered due to thermal decomposition when the pipe temperature is 120° C. On the other hand, regarding hexamethylenetriperoxidediamine, the detection sensitivity is high when the pipe temperature is 120° C., but the detection sensitivity is lowered due to the influence of adsorption onto the interior of the pipe when the pipe temperature is 70° C. In order to enable simultaneous detection of these substances, the sample introduction pipe 32 heated at 70° C. and the sample introduction pipe 33 heated at 120° C. are used. In the present embodiment, the two types for the low temperature and the high temperature have been explained as an example; however, more pipes may be further used.

When hexamethylenetriperoxidediamine is detected, gases or fine particles adsorb onto the pipe interior of the sample introduction pipe 32 heated at 70° C., and the interior is contaminated. In this case, the pipe has to be subjected to heating cleaning so that next detection can be promptly carried out. In this process, the temperatures opposite to those of the above description are set. Specifically, the set temperature of the pipe heater 34 which used to be at 70° C. is set to 120° C., the set temperature of the pipe heater 35 which used to be at 120° C. is set to 70° C., and heating is carried out. As a result, the pipe heater 34 undergoes heating cleaning at 120° C., and the temperature of the pipe heater 35 is lowered to 70° C. Normally, when heating cleaning is to be carried out, generally, they are heated at the set temperatures of both the pipe heater 34 and the pipe heater 35 increased to a temperature equal to or higher than 120° C., for example, to 150° C. However, in that case, the temperatures have to be increased and reduced, which takes time, and next detection cannot be carried out promptly. In the present embodiment, simply by reversing the set temperatures of the pipe heater 34 and the pipe heater 35, the temperature of the pipe heater 34 can be increased, and the temperature of the pipe heater 35 can be lowered at the same time. In this manner, time can be saved, and the next detection can be promptly carried out.

Figure 15:
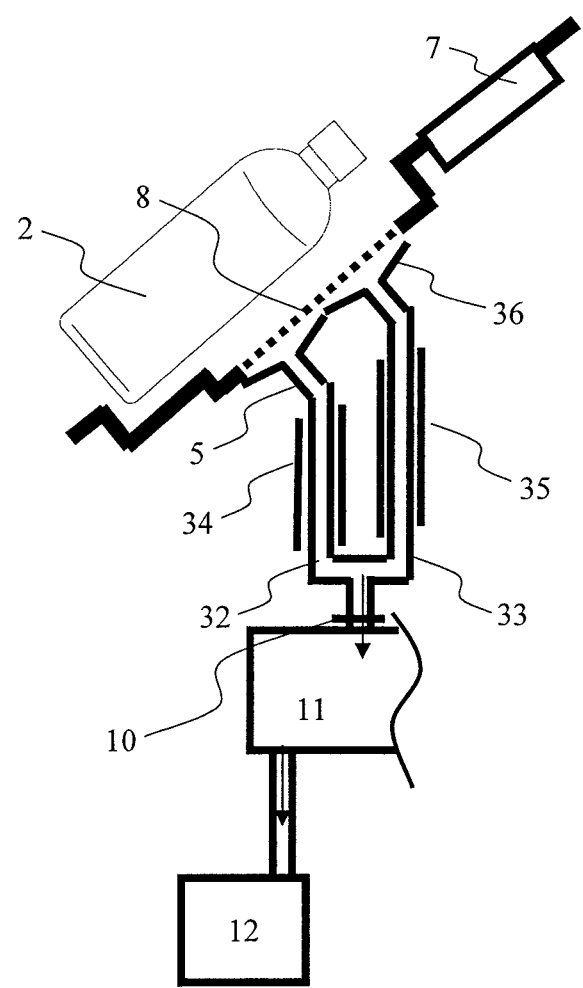
FIG. 15 is an explanatory drawing showing an example of the detection system having a plurality of introduction regions and a plurality of sample introduction pipes.

Not only the plurality of sample introduction pipes, but also a plurality of introduction regions can be used. FIG. 15 is an explanatory drawing showing an example of the detection system having a plurality of introduction regions and a plurality of sample introduction pipes. The gases and fine particles contained in the air near the cap of the bottle are introduced into the ion source 11 from the introduction region 5 and the introduction region 36 via the sample introduction pipe 32 and the sample introduction pipe 33. Although it is not shown in the figure, the introduction region 5 is heated to 70° C. by a heater, and the introduction region 36 is heated to 120° C. Not only the sample introduction pipes, but also the introduction regions are heated; as a result, adsorption and thermal decomposition can be further prevented. In the present embodiment, the introduction region is arranged in a longitudinal direction; however, the introduction regions may be provided in, for example, a transverse direction as long as gases and fine particles can be efficiently sucked-in. The size of the introduction regions may be changed.

DESCRIPTION OF SYMBOLS

1 Detection system
2 Bottle
3 Detection space (big bottle)
4 Detection space (small bottle)
5 Introduction region
6 Cap marker
7 Monitor
8 Rough mesh filter
9 Pipe heater
10 Fine mesh filter
11 Ion source
12 Intake pump
13 Mass analysis region
14 Data processor
15 Database region
16 Identification region
17 Sample introduction pipe
18 Needle electrode
19 Counter electrode
20a First aperture
20b Second aperture
20c Third aperture
21a First differential pumping region
21b Second differential pumping region
21c Vacuum region
22a Vacuum pump
22b Vacuum pump
23 Ion guide
24 Ion trap region
25a Inlet end lens
25b Outlet end lens
26 Quadrupole rods
27 Excitation electrodes
28a Trap wire
28b Extraction wire
29 Trap region
30 Detector
31 Gas supply unit
32 Sample introduction pipe
33 Sample introduction pipe
34 Pipe heater
35 Pipe heater
36 Introduction region

What is claimed is:

1. A dangerous substance detection system comprising:
a bottle placement space for placing a bottle to be detected;
an introduction region bored in the bottle placement space;
an intake region for sucking-in a sample gas from the introduction region;
an ion source for ionizing the sucked-in sample gas;
a mass analysis region for subjecting an ion generated by the ion source to mass analysis;
a data processor for controlling the ion source and the mass analysis region;
a database region for retaining mass spectrum data derived from a handmade explosive;
an identification region for collating the result of the mass analysis of the sample gas carried out by the mass analysis region with the mass spectrum data retained in the database region and determining presence/absence of the handmade explosive; and
a monitor for displaying the result of the determination carried out by the identification region;
wherein the introduction region and the ion source are connected to each other by a first sample introduction pipe and a second sample introduction pipe disposed in parallel to each other, and the first sample introduction pipe is heated to 50° C. to 120° C.

2. The dangerous substance detection system according to claim 1, wherein the ion source generates the ion by a corona discharge.

3. The dangerous substance detection system according to claim 1, wherein the identification region determines that triacetone triperoxide has been detected if the ion having at least one mass/charge ratio among mass/charge ratios of 33, 43, 75, and 77 is detected from the sample gas.

4. The dangerous substance detection system according to claim 1, wherein the identification region determines that hexamethylenetriperoxidediamine has been detected if the ion having at least one mass/charge ratio among mass/charge ratios of 145, 179, and 209 is detected from the sample gas.

5. The dangerous substance detection system according to claim 1, wherein the identification region determines that hydrogen peroxide has been detected if the ion having at least one mass/charge ratio among mass/charge ratios of 66 and 77 is detected from the sample gas.

6. The dangerous substance detection system according to claim 1, wherein the second sample introduction pipe is heated to 100° C. to 150° C.

7. A dangerous substance detection system comprising:
a bottle placement space for placing a bottle to be detected;
an introduction region bored in the bottle placement space;
an intake region for sucking-in a sample gas from the introduction region;
an ion source for ionizing the sucked-in sample gas;
a mass analysis region for subjecting an ion generated by the ion source to mass analysis;
a data processor for controlling the ion source and the mass analysis region so as to carry out tandem mass analysis;
a database region for retaining fragment mass spectrum data derived from a handmade explosive;
an identification region for collating the result of the tandem mass analysis of the sample gas carried out by the mass analysis region with the fragment mass spectrum data retained in the database region and determining presence/absence of the handmade explosive; and
a monitor for displaying the result of the identification region;
wherein
the tandem mass analysis is carried out while using the ion having a mass/charge ratio of 145 as a precursor ion; and
if the ion having a mass/charge ratio of 117 is detected in a fragment mass spectrum, the identification region determines that hexamethylenetriperoxidediamine has been detected.

8. The dangerous substance detection system according to claim 7, wherein the ion source generates the ion by a corona discharge.

9. The dangerous substance detection system according to claim 7, wherein the identification region determines that triacetone triperoxide has been detected if the ion having at least one mass/charge ratio among mass/charge ratios of 33, 43, 75, and 77 is detected from the sample gas.

10. The dangerous substance detection system according to claim 7, wherein the identification region determines that hexamethylenetriperoxidediamine has been detected if the ion having at least one mass/charge ratio among mass/charge ratios of 145, 179, and 209 is detected from the sample gas.

11. A dangerous substance detection system comprising:
a bottle placement space for placing a bottle to be detected;
an introduction region bored in the bottle placement space;
an intake region for sucking-in a sample gas from the introduction region;
an ion source for ionizing the sucked-in sample gas;
a mass analysis region for subjecting an ion generated by the ion source to mass analysis;
a data processor for controlling the ion source and the mass analysis region so as to carry out tandem mass analysis;
a database region for retaining fragment mass spectrum data derived from a handmade explosive;
an identification region for collating the result of the tandem mass analysis of the sample gas carried out by the mass analysis region with the fragment mass spectrum data retained in the database region and determining presence/absence of the handmade explosive; and
a monitor for displaying the result of the identification region;
wherein
the tandem mass analysis is carried out while using both of or either one of the ion having a mass/charge ratio of 66 and the ion having a mass/charge ratio of 77 as a precursor ion; and
the identification region determines that hydrogen peroxide has been detected:
if the ion having the mass/charge ratio of 66 is a precursor ion and if the ion having the mass/charge ratio of 48 is detected in a fragment mass spectrum or
if the ion having the mass/charge ratio 77 is a precursor ion and if the ion having a mass/charge ratio of 60 is detected in a fragment mass spectrum.

12. A dangerous substance detection system comprising:
a bottle placement space for placing a bottle to be detected;
an introduction region bored in the bottle placement space;
an intake region for sucking-in a sample gas from the introduction region;
an ion source for ionizing the sucked-in sample gas;
a mass analysis region for subjecting an ion generated by the ion source to mass analysis;
a data processor for controlling the ion source and the mass analysis region so as to carry out tandem mass analysis;
a database region for retaining fragment mass spectrum data derived from a handmade explosive;
an identification region for collating the result of the tandem mass analysis of the sample gas carried out by the mass analysis region with the fragment mass spectrum data retained in the database region and determining presence/absence of the handmade explosive; and
a monitor for displaying the result of the identification region;
wherein
the tandem mass analysis is carried out while using the ion having a mass/charge ratio of 75 as a precursor ion; and
the identification region determines that triacetone triperoxide has been detected if the ion having the mass/charge ratio of 75 is used as a precursor ion and if the ion having a mass/charge ratio of 48 is detected in a fragment mass spectrum.

13. The dangerous substance detection system according to claim 7, wherein the introduction region and the ion source are connected to each other by a sample introduction pipe, and the sample introduction pipe is heated to 50° C. to 150° C.

14. A dangerous substance detection method including:
a step of sucking-in a sample gas generated from a bottle to be detected;
a step of ionizing the sample gas;
a step of subjecting the ionized ion to mass analysis;
a step of collating a mass spectrum obtained as a result of the mass analysis, with mass spectrum data retained in a database and derived from a handmade explosive;
a step of determining presence/absence of a component substance of the handmade explosive based on the collation result; and
a step of displaying the result of the presence/absence determination;
wherein
the mass analysis is carried out while using the ion having a mass/charge ratio of 145 as a precursor ion; and
if the ion having a mass/charge ratio of 117 is detected in a fragment mass spectrum, the identification region determines that hexamethylenetriperoxidediamine has been detected.

* * * * *